(12) United States Patent
Gilkerson et al.

(10) Patent No.: US 6,678,560 B1
(45) Date of Patent: Jan. 13, 2004

(54) CARDIAC RHYTHM MANAGEMENT SYSTEM WITH ELECTROSURGERY MODE

(75) Inventors: James O. Gilkerson, Stillwater, MN (US); Vickie L. Conley, Woodbury, MN (US); Kristine M. Larsen-Kelly, Lino Lakes, MN (US); Allan Thomas Koshiol, Lino Lakes, MN (US); John William Gilliver, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/235,106

(22) Filed: Jan. 21, 1999

(51) Int. Cl.$^7$ ................................................ A61N 1/37
(52) U.S. Cl. ............................................ 607/14; 607/30
(58) Field of Search ...................................... 607/14, 30

(56) References Cited

U.S. PATENT DOCUMENTS

| | | | |
|---|---|---|---|
| 4,796,630 A | * | 1/1989 | Regna |
| 5,247,930 A | * | 9/1993 | Begemann et al. ............ 607/11 |
| 5,735,882 A | * | 4/1998 | Rottenberg et al. ............ 607/27 |

* cited by examiner

*Primary Examiner*—Carl H. Layno
(74) *Attorney, Agent, or Firm*—Schwegman, Lundberg, Woessner & Kluth, P.A.

(57) ABSTRACT

A cardiac rhythm management system includes an electrosurgery mode of operating an implantable cardiac rhythm management device, such as a pacemaker, defibrillator, or pacer/defibrillator. In electrosurgery mode, certain device parameters are programmed to particular electrosurgery mode values in order to increase the immunity of the implanted device to electromagnetic interference during electrosurgery. Electrosurgery mode device parameter values include both previously-programmed values and different values that are particular to electrosurgery mode. Electrosurgery mode is initiated by an external programmer, which enables electrosurgery mode parameters, displays an indicator to the user, and disables further device parameter programming until electrosurgery mode is terminated by a user request from the external programmer. Electrosurgery mode includes asynchronous pacing, such as DOO mode providing atrial and ventricular pacing at previously programmed rate, AV delay, amplitudes, and pulse widths. Sensing of intrinsic cardiac signals, sensor rate modulation, and tachyarrhythmia detection and therapy are all turned off during electrosurgery mode.

20 Claims, 3 Drawing Sheets

CARDIAC RHYTHM MANAGEMENT SYSTEM WITH ELECTROSURGERY MODE

FIELD OF THE INVENTION

This invention relates generally to cardiac rhythm management systems and particularly, to a cardiac rhythm management system with an electrosurgery mode.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias is via drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via a transvenous leadwire having one or more electrodes disposed in the heart. Heart contractions are initiated in response to such pace pulses. By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a countershock. The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other systems or devices for diagnosing or treating cardiac arrhythmias.

One problem that arises in implantable cardiac rhythm management devices is possible adverse consequences to such devices when a physician is performing electrosurgery on the patient in which the device is implanted. See Neil F. Strathmore, "Interference in Cardiac Pacemakers," (Kenneth A. Ellenbogen, G. Neal Kay, and Bruce L. Wilkoff, eds. "Clinical Cardiac Pacing," 1st ed., pp. 772–73 (1995)). Electrosurgery includes electrocautery, diathermy, and radio-frequency (RF) ablation. Electrosurgery uses electromagnetic energy, such as RF currents, to cut, coagulate, and/or congeal the patient's tissue. For example, RF ablation is used to modify the conduction paths of intrinsic heart signals through cardiac tissue in order to treat cardiac arrhythmias. There are many other applications of electrosurgery.

The RF signals used in performing electrosurgery may interfere with proper operation of the implanted cardiac rhythm management device, particularly if the electrosurgical electrodes are used near the implanted device. For example, circuits in the implanted device that sense intrinsic heart signals may interpret an RF electrosurgery signal as an intrinsic cardiac depolarization. In response, the implanted device may be inhibited from delivering a needed pacing pulse. In other implanted devices, the RF electrosurgery signals may cause the implanted device to revert to a backup/reset/startup mode of operation. The implanted cardiac rhythm management device will not return to normal operation until the implanted device is reprogrammed via an external programmer. This can cause hemodynamic compromise if the backup parameters are inadequate for the particular patient in which the cardiac rhythm management device is implanted.

Some implanted devices may be vulnerable to reprogramming by the RF electrosurgery signal itself when a magnet is applied during the electrosurgery procedure to ensure asynchronous pacing (i.e., ignoring sensed intrinsic heart signals) during the electrosurgery procedure. Such reprogramming by the RF electrosurgery signal may leave the patient without adequate cardiac rhythm management therapy, or may even result in the delivery of inappropriate therapy by the RF-reprogrammed implanted device. Thus, there is a need to reduce the risk of adverse interactions between an implanted cardiac rhythm management device and an electrosurgical instrument being used on a patient in which the device is implanted.

SUMMARY

The present system provides a cardiac rhythm management system including an implantable cardiac rhythm management device having an electrosurgery state, also referred to as an electrosurgery mode. The electrosurgery mode programs certain device parameters to particular electrosurgery mode values in order to increase the immunity of the implanted device to interference resulting from the electrosurgery. Some of the electrosurgery mode device parameter values use corresponding previously programmed values from a normal mode of operation. Others of the electrosurgery mode device parameter values may be different from the corresponding previously programmed values from the normal mode of operation.

The present cardiac rhythm management system allows a user to use an external programmer to initiate an electrosurgery mode in an implanted cardiac rhythm management device, where the device parameter values used in the electrosurgery mode are both safe for use during electrosurgery and provide effective therapy to the patient, at least insofar as certain of the previously programmed device parameters were tailored for providing effective therapy to the patient.

In one embodiment, the cardiac rhythm management (CRM) system includes an external programmer and an implantable CRM device. The CRM device includes an electrosurgery state initiated by a first command received from the external programmer. Initiation of the electrosurgery state results in a request for confirmation from the user of the external programmer, identification of the electrosurgery state to the user of the external programmer, and the disabling of further programming of bradyarrhythmia and tachyarrhythmia parameters until the electrosurgery state is exited by a second command received from the external programmer. During the electrosurgery state both bradyarrhythmia and tachyarrhythmia mode device parameters are programmed to particular values corresponding to electrosurgery mode. The device is configured to deliver asynchronous pacing (e.g., pacing mode set to DOO, AOO, VOO, etc.). In one example, a pacing mode is set to DOO, providing atrial and ventricular pacing, deactivating sensing of atrial and ventricular intrinsic heart signals, and providing no pacing therapy in response to the atrial and ventricular intrinsic heart signals. A pacing rate, a fixed atrial-ventricular (AV) delay, atrial and ventricular pacing amplitudes, and atrial and ventricular pacing pulse widths are each set to a corresponding value programmed prior to initiation of the electrosurgery state. Tachyarrhythmia sensing and therapy are disabled. Aspects of the present cardiac rhythm management system, including its electrosurgery mode, are presented in the following detailed description of the invention and the corresponding drawings that form a part thereof.

BRIEF DESCRIPTION OF THE DRAWINGS

In the drawings, like numerals describe substantially similar components throughout the several views.

DETAILED DESCRIPTION

Figure 1:
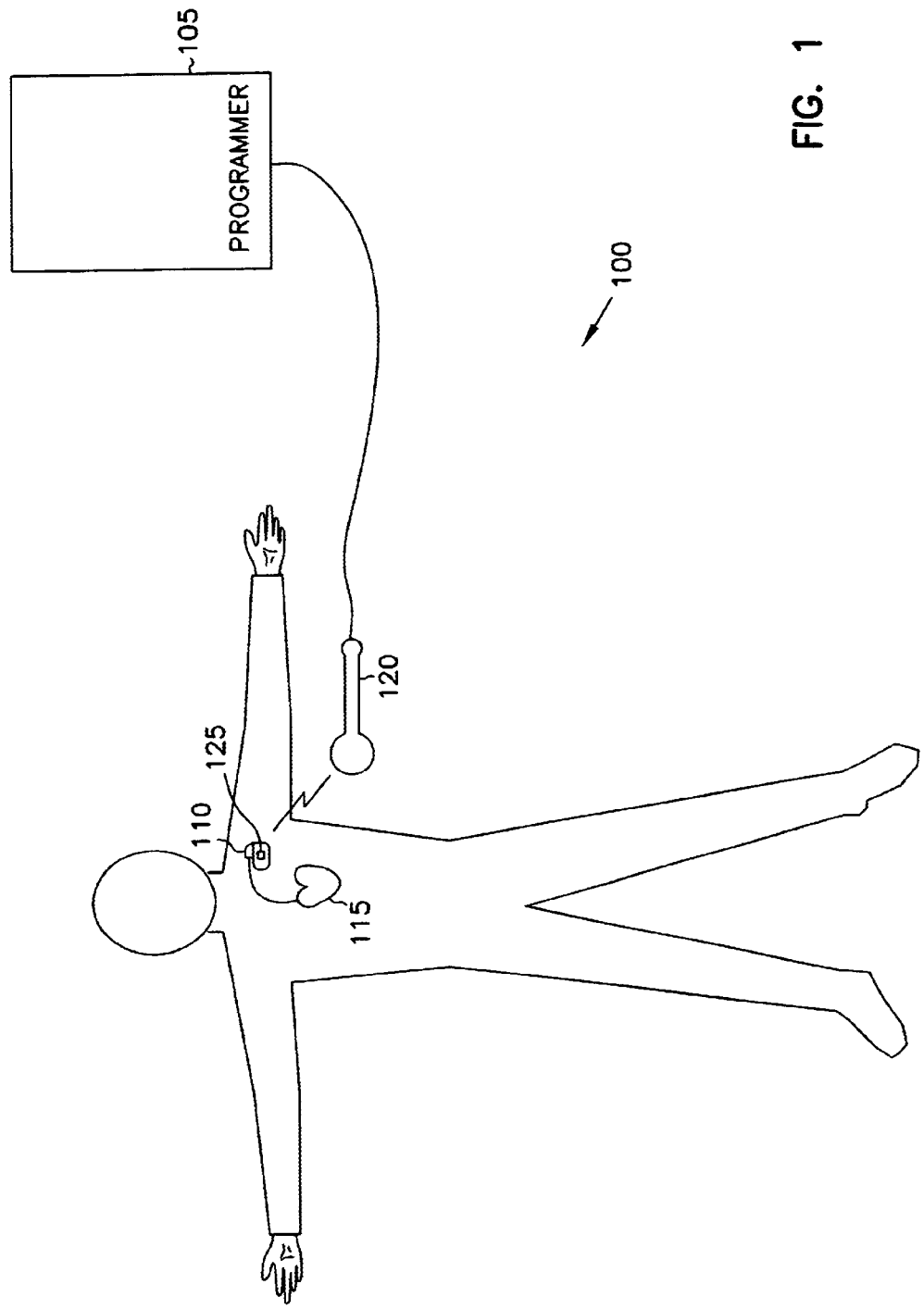
FIG. 1 is a schematic/block diagram illustrating portions of the present cardiac rhythm management system and an environment in which it is used.

In the drawings that accompany the following detailed description, like numerals describe substantially similar components throughout the several views.

FIG. 1 is a schematic/block diagram illustrating portions of the present cardiac rhythm management system and an environment in which it is used. In FIG. 1, cardiac rhythm management system 100 includes an external programmer 105 and an implanted cardiac rhythm management device 110, such as a pacer, a defibrillator, or a pacer/defibrillator. The implanted device 110 is coupled to heart 115, such as by one or more leadwires or otherwise, for delivering cardiac rhythm management therapy (e.g., electrical pulses or defibrillation countershocks). A communication device, such as telemetry device 120, communicatively couples external programmer 105 to implanted device 110.

Implanted device 110 includes a microprocessor, state machine, or other controller 125 that includes a memory in which various device parameters are stored. Such device parameters control operation of various electronic circuits in implanted device 110, so that appropriate cardiac rhythm management therapy is delivered to the patient. Some of these device parameters can be programmed by the physician, by using the external programmer 105, so that the cardiac rhythm management therapy delivered by the implanted device 11 is tailored to meet the needs and alleviate the symptoms of the particular patient in which device 110 is implanted.

Figure 2:
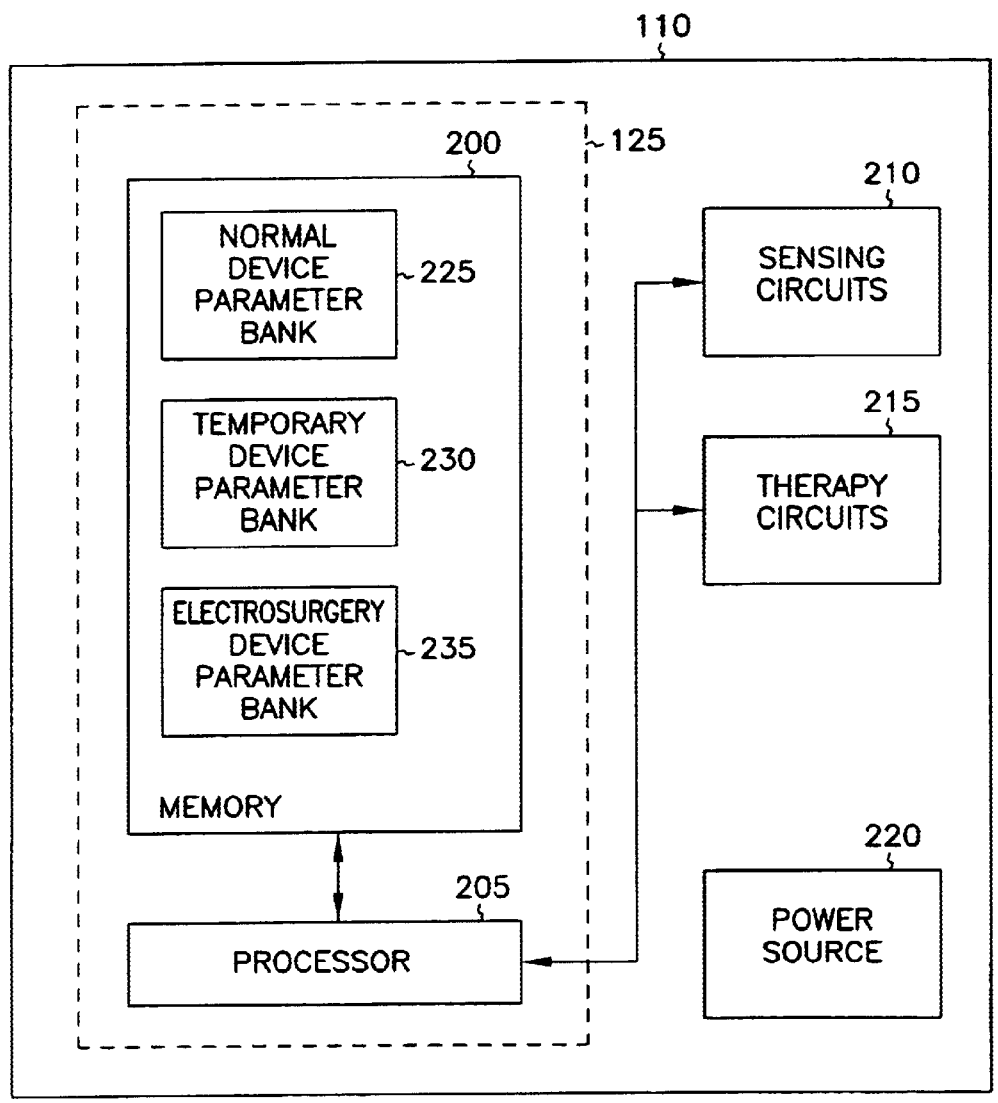
FIG. 2 is a generalized block diagram illustrating portions of an implanted cardiac rhythm management device.

FIG. 2 is a generalized block diagram illustrating portions of implanted device 110, including controller 125 having memory 200 and processor 205, sensing circuits 210, therapy storage and delivery circuits 215, and power source 220. Memory 200 includes a normal device parameter bank 225, a temporary device parameter bank 230, and an electrosurgery device parameter bank 235, corresponding to normal, temporary, and electrosurgery states/modes of operation, respectively.

The attending physician may use external programmer 105 to program implanted device 110 from the normal mode of operation to the temporary mode of operation, which uses a temporary set of parameters stored in temporary device parameter bank 230. This is useful, for example, in determining whether a particular trial set of device parameters is providing appropriate therapy to the patient, in temporary mode, before actually selecting such parameters for use in the normal mode. While the effects of the temporary device parameters are being investigated, the normal device parameters are saved in a separate memory location, such as normal device parameter bank 225. When the physician uses the external programmer 105 to exit the temporary mode of operation, implanted device 110 resumes use of the previously-saved normal device parameters. In order to maximize the usefulness of the temporary mode of operation as a diagnostic and clinical tool, the physician is allowed to experiment with a wide variety of possible of device parameter values in the temporary mode of operation (e.g., allowing sensing of intrinsic heart signals and inhibiting the delivery of pace pulses if cardiac depolarizations are detected, using rate-responsive pacing behavior, sensing tachyarrhythmias and delivering anti-tachyarrhythmia pacing (ATP) or electrical defibrillation countershock therapy).

Figure 3:
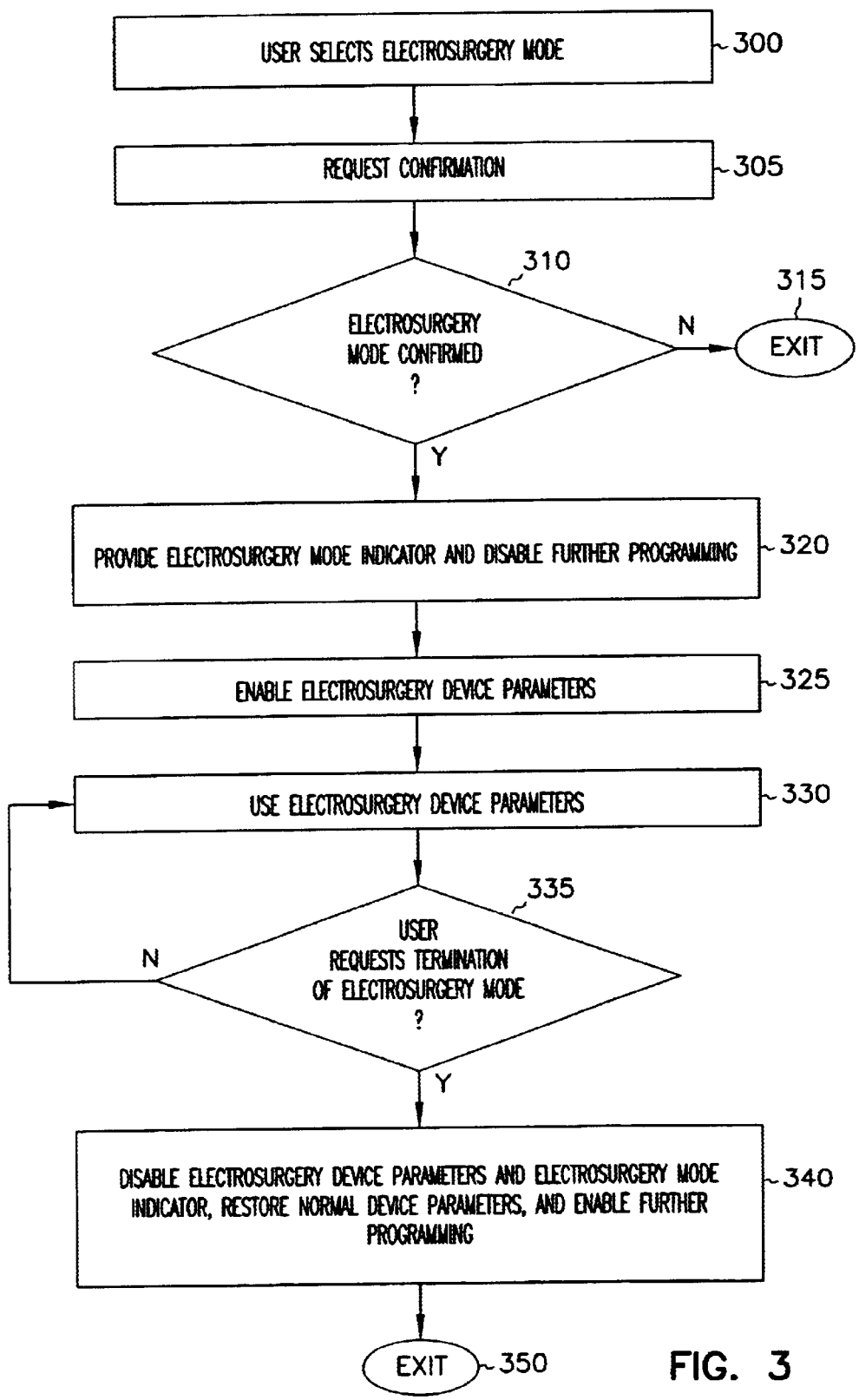
FIG. 3 is a flow chart illustrating use of an electrosurgery mode of operating a cardiac rhythm management system.

The user may also use external programmer 105 to program implanted device 110 from the normal mode of operation, into the electrosurgery mode of operation, as illustrated in the flow chart of FIG. 3. At step 300, the user selects the electrosurgery mode using external programmer 105. At step 305, external programmer 105 requests confirmation from the user that electrosurgery mode is desired. If the user does not confirm, at step 310, that electrosurgery mode is desired, the illustrated set of actions are exited at step 315. If, however, the user confirms, at step 310, that electrosurgery mode is desired, external programmer 105 provides an electrosurgery mode indicator (e.g., via a display on external programmer 105) to the user, at step 320, to indicate that implanted device 110 is being initiated into electrosurgery mode.

At step 325, electrosurgery device parameters are enabled. This includes programming parameter values associated with both bradycardia and tachycardia modes of operation. The device is configured to deliver asynchronous pacing (e.g., pacing mode is set to DOO, AOO, VOO, etc., such that the pacing pulses are delivered without synchronizing to detected intrinsic electrical heart activity signals). In one example, a pacing mode is set to DOO (pacing mode codes are defined by the North American Society of Pacing and Electrophysiology (NASPE) and the British Pacing and Electrophysiology Group (BPEG), see, e.g., Ellenbogen, Kay, and Wilkoff, supra at 567). In DOO mode, device 110 provides asynchronous atrial and ventricular pacing. Sensing of atrial and ventricular intrinsic heart signals is deactivated, thus no pacing therapy is provided in response to the atrial and ventricular intrinsic heart signals. Sensor-controlled rate modulation is turned off. A pacing rate is set to a corresponding previously programmed lower rate limit value, that is, the lower rate limit value from the normal mode of operation. Similarly, a fixed atrial-ventricular delay is set to a corresponding previously programmed fixed AV delay value used in the normal mode of operation. Atrial and ventricular pacing amplitudes, and atrial and ventricular pacing pulse widths are also each set to corresponding values programmed prior to initiation of the electrosurgery state, that is, the corresponding values from the normal mode of operation. Tachyarrhythmia sensing and tachyarrhythmia therapy delivery are also deactivated during electrosurgery mode.

At step 330, the above-described electrosurgery mode device parameters are used in device 110 while electrosurgery is being performed on the patient in which device 110 is implanted. Use of these electrosurgery mode device parameters continues until the user requests termination of electrosurgery mode, using external programmer 105, at step 335. If the user requests termination of electrosurgery mode at step 335, then at step 340 the electrosurgery mode device parameters are disabled, the electrosurgery mode indicator on external programmer 105 is turned off, and external programmer 105 enables further programming of normal mode device parameters, before the illustrated set of actions are exited at step 350.

What is claimed is:

1. A cardiac rhythm management (CRM) system including:
    an external programmer; and
    an implantable CRM device, the CRM device including an electrosurgery state initiated by a first command received from the external programmer, the electrosurgery state including:
        a bradyarrhythmia mode having bradyarrhythmia parameters including:
            a pacing mode that is set to deliver asynchronous pacing, providing atrial and ventricular pacing, deactivating sensing of atrial and ventricular intrinsic heart signals, and providing no pacing therapy in response to the atrial and ventricular intrinsic heart signals; and
            a pacing rate, a fixed atrial-ventricular (AV) delay, atrial and ventricular pacing amplitudes, and atrial and ventricular pacing pulse widths that are each set to a corresponding value programmed prior to initiation of the electrosurgery state;
        a tachyarrhythmia mode having tachyarrhythmia parameters including:
            a tachyarrhythmia sensing state that is deactivated; and
            a tachyarrhythmia therapy state that is disabled; and
    wherein at the initiation of the electrosurgery state the external programmer requests confirmation from a user of the external programmer, the external programmer identifies the electrosurgery state to the user of the external programmer, and the external programmer disables further programming of the bradyarrhythmia and tachyarrhythmia parameters until the electrosurgery state is exited by a second command received from the external programmer.

2. The system of claim 1, wherein the CRM device includes a temporary device parameter bank.

3. The system of claim 1, wherein the CRM device includes a normal device parameter bank.

4. The system of claim 1, wherein the CRM device contains separate memory locations to store the pacing parameters that correspond to the electrosurgery state.

5. The system of claim 1, wherein the CRM device includes therapy storage and delivery circuits.

6. An implantable cardiac rhythm management (CRM) system, the CRM system including:
    an external programmer;
    an implantable CRM device, the CRM device including an electrosurgery state initiated by a first command received from the external programmer, the electrosurgery state including:
        a bradyarrhythmia mode; and
        a tachyarrhythmia mode;
    wherein at the initiation of the electrosurgery state the external programmer requests confirmation from a user of the external programmer, the external programmer identifies the electrosurgery state to the user of the external programmer, and the external programmer disables further programming of the bradyarrhythmia and tachyarrhythmia parameters until the electrosurgery state is exited by a second command received from the external programmer.

7. The system of claim 6, wherein the the bradyarrhythmia mode includes bradyarrhythmia parameters including at least:
    a pacing mode that is set to deliver asynchronous pacing, providing atrial and ventricular pacing, deactivating sensing of atrial and ventricular intrinsic heart signals, and providing no pacing therapy in response to the atrial and ventricular intrinsic heart signals; and
    a pacing rate, a fixed atrial-ventricular (AV) delay, atrial and ventricular pacing amplitudes, and atrial and ventricular pacing pulse widths that are each set to a corresponding value programmed prior to initiation of the electrosurgery state.

8. The system of claim 7, wherein the CRM device includes a temporary device parameter bank.

9. The system of claim 7, wherein the CRM device includes a normal device parameter bank.

10. The system of claim 7, wherein the CRM device contains separate memory locations to store the pacing parameters that correspond to the electrosurgery state.

11. The system of claim 7, wherein the CRM device includes therapy storage and delivery circuits.

12. The system of claim 7, wherein the tachyarrhythmia mode has tachyarrhythmia parameters including:
    a tachyarrhythmia sensing state that is deactivated; and
    a tachyarrhythmia therapy state that is disabled.

13. An apparatus for programming a CRM device, comprising:
    a programmer memory for storing data;
    a keypad for entry of parameters for an electrosurgery state of the CRM device for storage in locations in the programmer data memory;
    a display to request confirmation from a user and to indicate that the CRM device is in the electrosurgery state;
    a transceiver to selectively upload data from the CRM device, or download the parameters for an electrosurgery state stored in the programmer memory to the CRM device, wherein the variables are stored in memory locations in the CRM device; and
    a processor connected to the transceiver, wherein the processor prevents further programming when the CRM device has been programmed into the electrosurgery state.

14. The apparatus of claim 13, wherein the external programmer enables the electrosurgery state with a single key press.

15. The apparatus of claim 13, wherein the external programmer display indicating the CRM device is in the electrosurgery state is cleared when the user terminates the electrosurgery state.

16. A method for a user of an external programmer, comprising:

instructing the external programmer to program a cardiac rhythm management (CRM) device into an electrosurgery state of operation upon confirmation from the user;

enabling parameters for the electrosurgery state in the CRM device after the confirmation;

indicating to the user that the CRM device is in the electrosurgery state;

prohibiting further programming of the CRM device until the user requests to terminate the electrosurgery state; and returning the CRM to normal bradyarrhythmia and tachyarrhythmia mode when requested by the user.

17. The method of claim 16, further comprising programming a DOO pacing mode.

18. The method of claim 16, wherein a single key depression by the user on the external programmer confirms the request for the electrosurgery state and enables the electrosurgery parameters.

19. The method of claim 18, wherein the parameters for the electrosurgery state in the CRM device are programmed prior to initiation of the electrosurgery state.

20. The method of claim 19, further comprising programming a DOO pacing mode.

* * * * *